US008877140B2

(12) United States Patent  
Chen et al.

(10) Patent No.: US 8,877,140 B2  
(45) Date of Patent: *Nov. 4, 2014

(54) COLOR-BASED REACTION TESTING OF BIOLOGICAL MATERIALS

(71) Applicant: Teco Diagnostics, Anaheim, CA (US)

(72) Inventors: Stephen L. Chen, Anaheim, CA (US); K C Chen, Anaheim, CA (US); Neeraj Kapoor, Anaheim, CA (US)

(73) Assignee: Teco Diagnostics, Anaheim, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/914,194

(22) Filed: Jun. 10, 2013

(65) Prior Publication Data

US 2013/0273666 A1    Oct. 17, 2013

Related U.S. Application Data

(63) Continuation of application No. 13/288,900, filed on Nov. 3, 2011, now Pat. No. 8,506,901.

(60) Provisional application No. 60/409,922, filed on Nov. 3, 2010, provisional application No. 61/410,207, filed on Nov. 4, 2010.

(51) Int. Cl.
| | |
|---|---|
| *G01N 33/00* | (2006.01) |
| *G01N 21/84* | (2006.01) |
| *G01N 21/78* | (2006.01) |
| *B01L 3/00* | (2006.01) |
| *A61B 10/00* | (2006.01) |
| *A61B 5/145* | (2006.01) |

(52) U.S. Cl.
CPC ......... *G01N 21/78* (2013.01); *B01L 2400/0457* (2013.01); *A61B 2010/0006* (2013.01); *B01L 2300/0832* (2013.01); *G01N 21/8483* (2013.01); *B01L 2300/042* (2013.01); *A61B 10/0064* (2013.01); *A61B 10/007* (2013.01); *B01L 2300/024* (2013.01); *B01L 2300/046* (2013.01); *A61B 5/14546* (2013.01); *B01L 3/5023* (2013.01); *B01L 2200/026* (2013.01); *B01L 2300/027* (2013.01); *B01L 2300/023* (2013.01); *A61B 5/14539* (2013.01); *A61B 10/0051* (2013.01); *A61B 2562/0295* (2013.01)
USPC ........... 422/402; 422/400; 422/401; 422/430; 422/68.1; 422/561

(58) Field of Classification Search
USPC ................. 422/400, 401, 402, 430, 68.1, 561
See application file for complete search history.

(56) References Cited

U.S. PATENT DOCUMENTS

| | | |
|---|---|---|
| 4,976,923 A | 12/1990 | Lipsky et al. |
| 5,119,830 A | 6/1992 | Davis |

(Continued)

OTHER PUBLICATIONS

International Search Report dated Dec. 30, 2011 (Four (4) pages).

(Continued)

*Primary Examiner* — Sam P Siefke  
(74) *Attorney, Agent, or Firm* — Crowell & Moring LLP

(57) ABSTRACT

A biological material test strip and adjacently-located reference color chart are affixed to a lid portion of an all-in-one specimen cup to perform color-based reaction testing of collected biological specimens in an uncalibrated environment. After specimen collection, the lid portion is secured to a container portion of the specimen cup. The cup may then be rotated into an upside down position causing the specimen, under the force of gravity, to pass from the container portion and into a volume of the lid portion, such that the test strip is exposed to the specimen as it is received into the volume of the lid portion. An image of the exposed test strip and adjacently-located reference color chart may then be captured and processed to identify any color matches between the individual test pads on the test strip and the corresponding sequences of reference color blocks on the reference chart.

9 Claims, 10 Drawing Sheets  
(7 of 10 Drawing Sheet(s) Filed in Color)

(56) References Cited

U.S. PATENT DOCUMENTS

| | | |
|---|---|---|
| 5,408,535 A | 4/1995 | Howard, III et al. |
| 5,501,837 A | 3/1996 | Sayles |
| 5,595,187 A | 1/1997 | Davis |
| 5,976,469 A | 11/1999 | Davis |
| 6,514,461 B1 | 2/2003 | Lappe et al. |
| 6,565,814 B1 | 5/2003 | Anraku et al. |
| 7,267,799 B1 | 9/2007 | Borich et al. |
| 7,292,718 B2 | 11/2007 | Douglass |
| 7,420,663 B2 | 9/2008 | Wang et al. |
| 7,652,268 B2 | 1/2010 | Patel |
| 2003/0108450 A1 | 6/2003 | Mainquist et al. |
| 2005/0221504 A1 | 10/2005 | Petruno et al. |
| 2007/0026530 A1 | 2/2007 | Wu et al. |
| 2008/0287316 A1 | 11/2008 | Spivey et al. |

OTHER PUBLICATIONS

International Search Report dated May 21, 2012 (Five (5) pages).

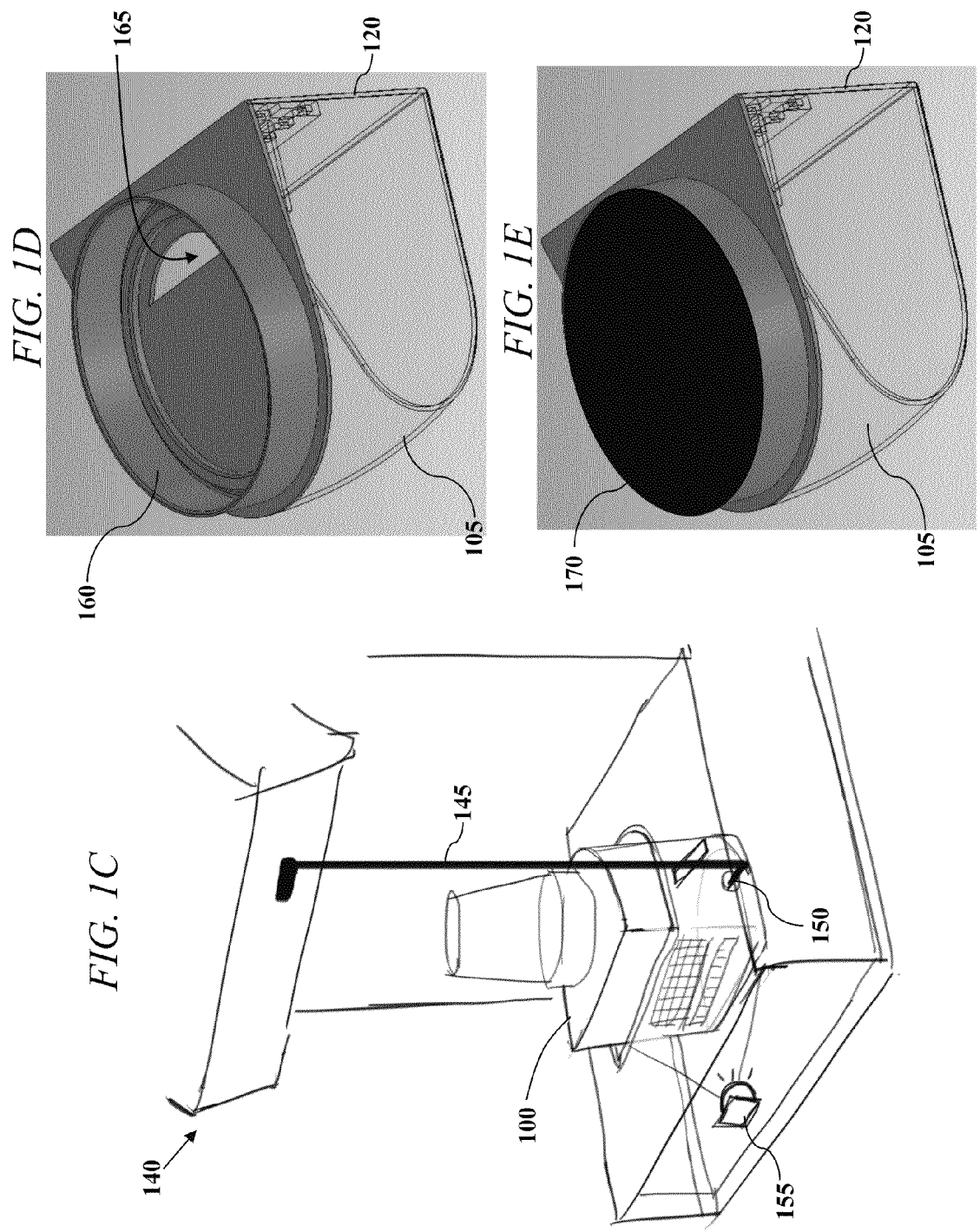

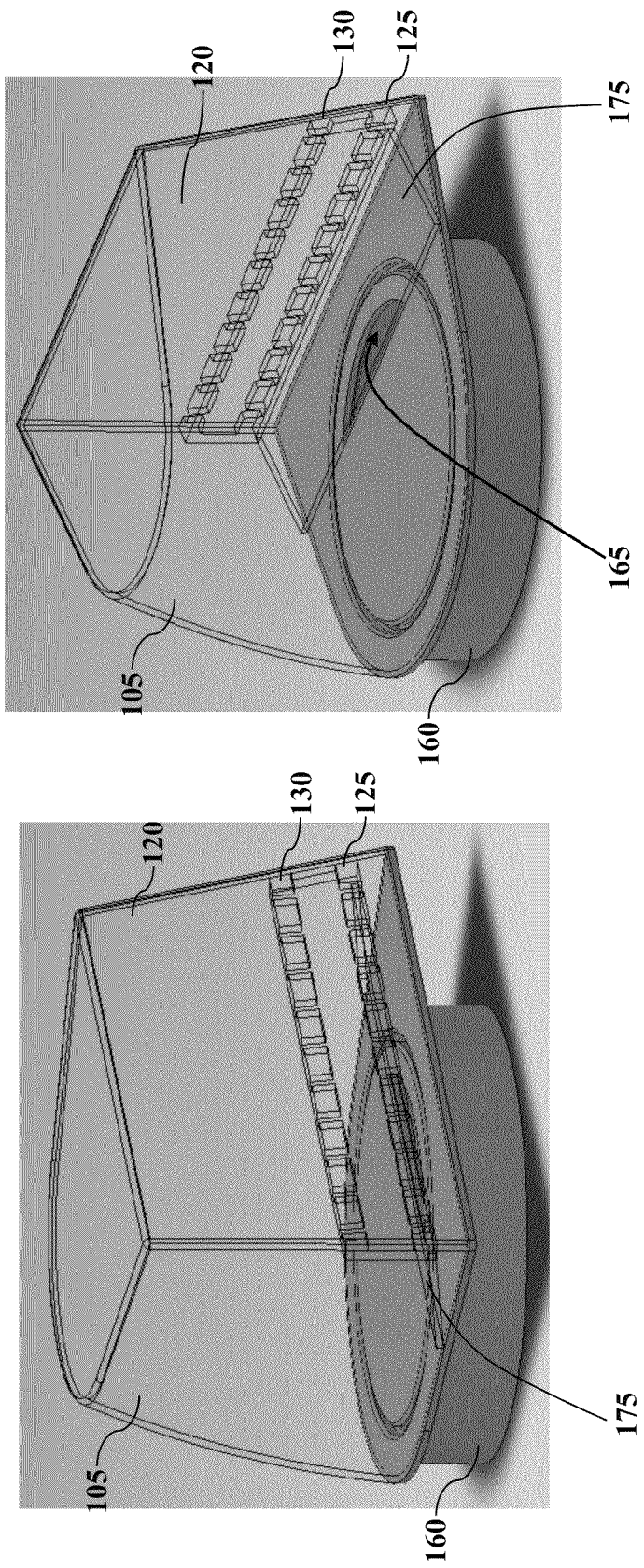

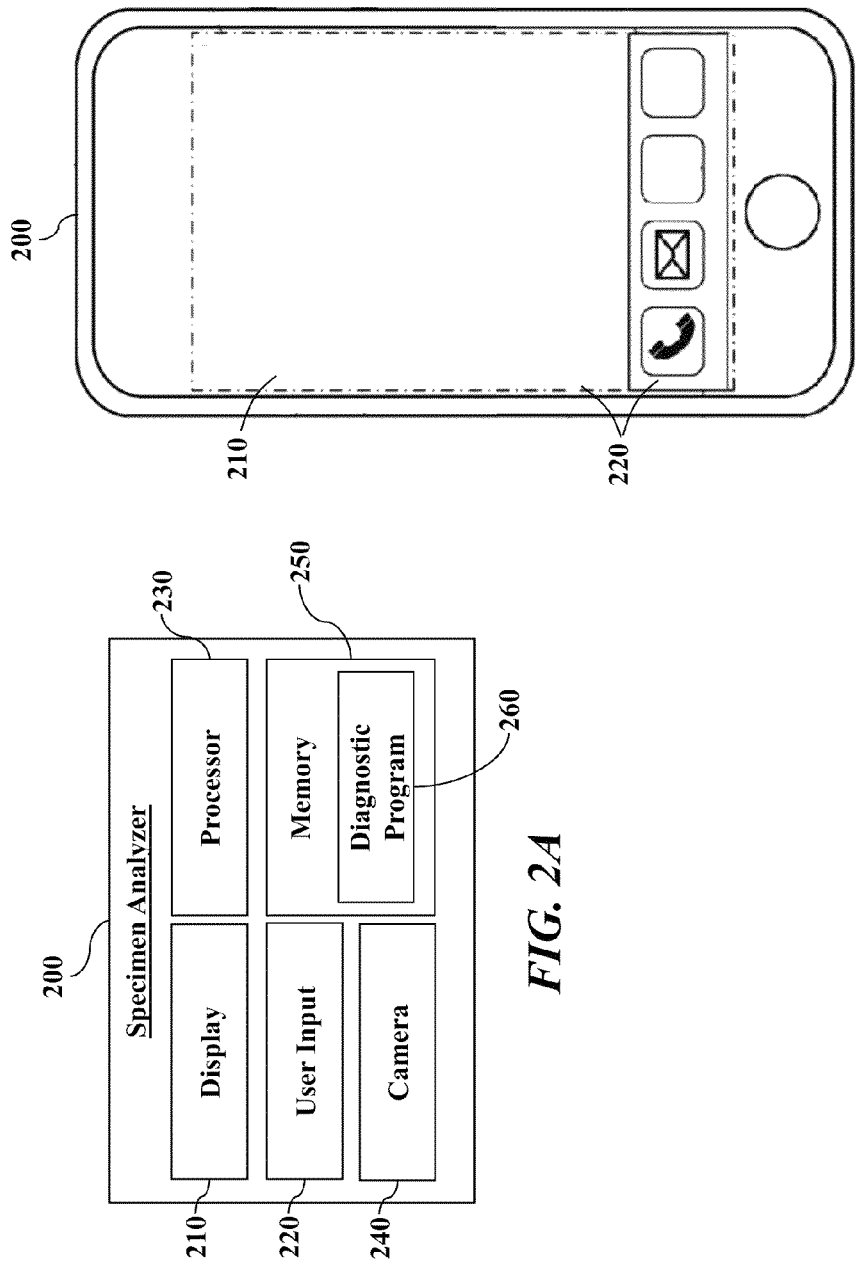

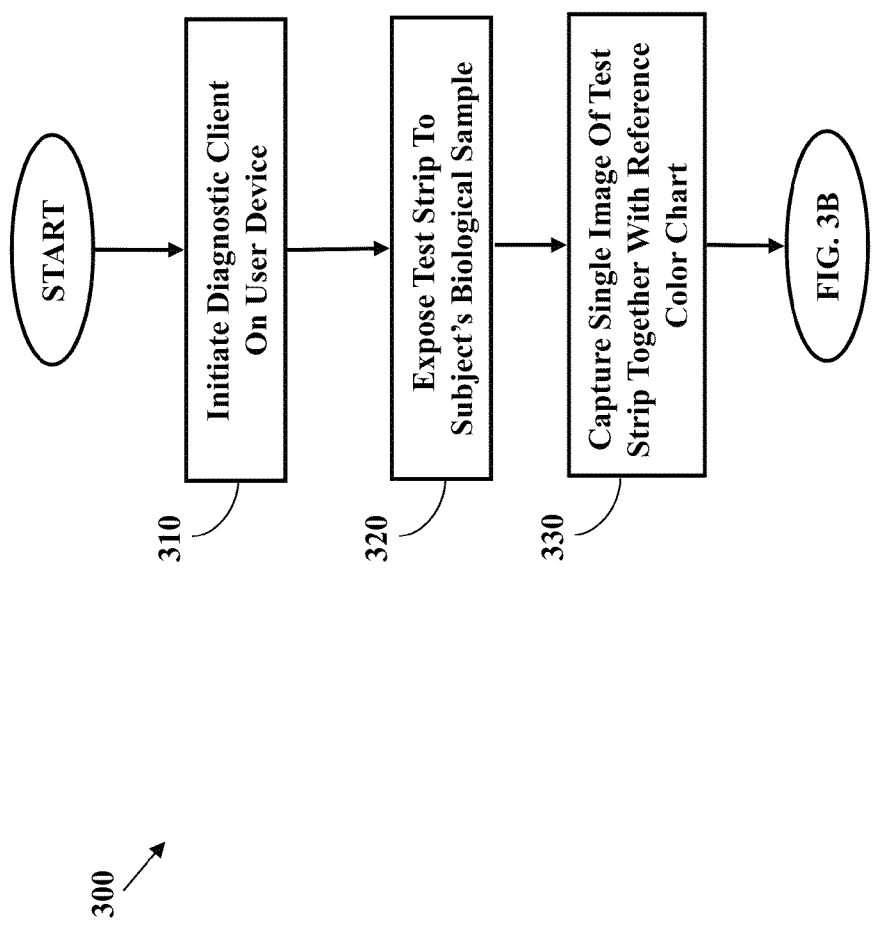

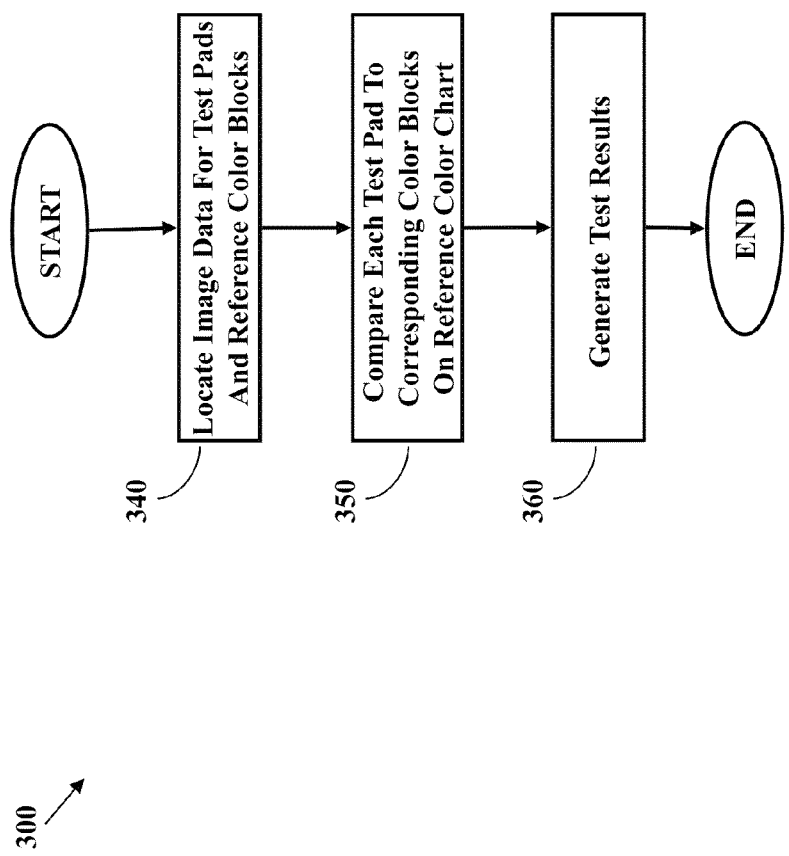

| Past Results | Patient ID: 355 | |
|---|---|---|
| LEUKOCYTES | | Negative |
| NITRITE | | Positive (++) |
| URO-BILINOGEN | | 0.2 (Normal) |
| PROTEIN | | Trace |
| PH | | 6.5 |
| BLOOD | | Small (+) |
| SPECIFIC GRAVITY | | 1.020 |
| KETONE | | Negative |

COLOR-BASED REACTION TESTING OF BIOLOGICAL MATERIALS

CROSS-REFERENCE TO RELATED APPLICATION

This application is a continuation of application Ser. No. 13/288,900, filed Nov. 3, 2011, which claims the benefit of U.S. Provisional Application No. 60/409,922, filed on Nov. 3, 2010, and also claims the benefit of U.S. Provisional Application No. 61/410,207, filed on Nov. 4, 2010.

FIELD OF THE INVENTION

The present invention relates generally to analyzing biological materials (e.g., urine, blood, saliva, feces, sweat and other biological materials) and more particularly to an all-in-one specimen cup that can be used for collecting biological materials, such as urine, and for performing color-based reaction testing of such biological materials using the same cup used to collect the specimen.

BACKGROUND OF THE INVENTION

Testing of biological materials may include the use of color-based reaction testing, whereby a test pad is exposed to urine, blood, saliva, feces or sweat. For example, urinalysis is an array of tests performed on urine and one of the most common methods of medical diagnosis. Urinalysis is used as a screening and/or diagnostic tool by virtue of being able to detect substances or cellular material in the urine associated with different metabolic and kidney disorders. For example, substances such as protein or glucose will begin to appear in the urine before patients are aware that they may have a problem.

Color-based reaction testing, such as urinalysis, is typically performed using "dipsticks," which are strips of plastic or sturdy paper to which a series of reagent test pads have been affixed. Each reagent test pad on the dipstick is chemically treated with a compound that is known to change color in the presence of particular reactants. For example, in the context of urinalysis, the dipstick will typically include reagent pads for detecting or measuring glucose, bilirubin, ketone (acetoacetic acid), specific gravity, blood, pH, protein, nitrite and leukocytes.

The process of testing biological materials involves first submerging or otherwise exposing the aforementioned dipsticks and affixed reagent pads to a subject's urine, saliva, blood, feces, or sweat. If the urine contains quantities of the particular reactants, one or more of the reagent test pads will change color as a result. The magnitude of the change is further indicative of the amount of the particular reactants that are present.

Urinalysis dipsticks, for example, are typically accompanied with a reference color chart for evaluating test pad color changes following exposure to urine. The typical reference color chart will include a spectrum of possible colors associated with each corresponding reagent pad on the dipstick, thereby allowing a healthcare provider to "read" the test results with the naked eye. However, manually comparing different shades of a given color can be difficult to perform and lead to unacceptably lower accuracy. Thus, it is preferable for healthcare providers to use a specialized electronic reader to eliminate the subjectivity of visual color interpretation, thereby making the color-based reaction testing process simpler and more reliable. Such electronic readers are highly-calibrated devices that typically use either reflectance photometers or charge coupled device (CCD) image sensors. Specifically, the image-capturing environment has to be precisely controlled across different tests since even slight variations in ambient light, test pad location or image-capturing angle can lead to inaccurate results. Moreover, there is even substantial variation across different CCD sensors meaning that each reader has to be individually calibrated.

There are several drawbacks with the prior art electronic readers. For example, they are complex and highly calibrated devices that are typically too expensive for most smaller laboratories to use. Moreover, since they have to be so highly calibrated, such prior art devices are closed, non-mobile devices, meaning that the resulting test data is not readily portable and that the actual test has to be performed wherever the electronic reader happens to be located. Additionally, the use of both collection cups and separate individual test strips is inconvenient and difficult to administer, whether in the home by the patient or in a high-volume laboratory where efficiently processing patient samples is at a premium. Therefore, there is a need to provide a more accurate and/or convenient alternative to performing color-based reaction testing of such biological materials.

SUMMARY OF THE INVENTION

Disclosed and claimed herein is an all-in-one cup and method of performing color-based reaction testing of biological materials using the all-in-one cup. In one embodiment, the all-in-one cup comprises a container portion configured to receive a biological specimen, and a lid portion having a flat side and being attachable to the container portion. The lid portion has a volume to receive the biological specimen under at least a force of gravity, and further includes a base with a hole disposed therein. The all-in-one cup also includes a color-based reaction test strip having a plurality of test pads and being affixed to an inner surface of the flat side of the lid portion. The all-in-one cup further includes a reference color chart affixed on either the inner surface or an outer surface of the flat side of the lid portion in an area adjacently-located to the test strip. The all-in-one specimen cup is configured to pass the biological specimen, at least under the force of gravity in response to being turned upside down, from the container portion through the hole in the base of the lid portion such that the test strip is exposed to the biological specimen as it is received into the volume of the lid portion.

Additionally, the disclosed and claimed method of performing color-based reaction testing of biological materials using the above-described all-in-one specimen cup includes capturing digital image information of an exposed test strip and the reference color chart in an uncalibrated environment, where the exposed test strip is the test strip affixed to the inner surface of the lid portion of the all-in-one specimen cup after being exposed to the biological specimen. The method also includes locating first image data (having color information) within the digital image information corresponding to each of the plurality of test pads. The method then includes locating second image data (also having color information) within the digital image information corresponding to each of the plurality of color blocks on the reference color chart. Finally, the method includes matching color information from the first image data to corresponding color information from the second image data, and generating test results based on such matching operation.

Also disclosed and claimed herein is a method of performing color-based reaction testing of biological materials using an all-in-one specimen cup, which includes providing a biological specimen into a container portion of the all-in-one specimen cup, and then securing a lid portion to the container portion, where the lid portion has a volume to receive the biological specimen under at least a force of gravity through a hole disposed in a base of the lid portion. The lid portion further includes a color-based reaction test strip, having a plurality of test pads, affixed to an inner surface of a flat side of the lid portion, and also includes a reference color chart affixed on either the inner surface or an outer surface of the flat side of the lid portion in an area adjacently-located to the test strip. The method further includes rotating the all-in-one cup until to an upside down position, thereby causing the biological specimen, under the force of gravity, to pass from the container portion through the hole in the base of the lid portion such that the test strip is an exposed test strip by virtue of coming into contact with the biological specimen as it is received into the volume of the lid portion. Thereafter, the method includes capturing digital image information of the exposed test strip and the reference color chart in an uncalibrated environment, and then locating first image data (having color information) within the digital image information corresponding to each of the plurality of test pads, and locating second image data (having color information) within the digital image information corresponding to each of the plurality of color blocks on the reference color chart. The color information from the first image data may then be matched to corresponding color information from the second image data, and test results generated based on such matching operation.

Other aspects, features, and techniques of the invention will be apparent to one skilled in the relevant art in view of the following description of the exemplary embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects, and advantages of the present invention will become more apparent from the detailed description set forth below when taken in conjunction with the drawings in which like reference characters identify correspondingly throughout, and wherein:

FIG. 1C depicts the all-in-one specimen cup of FIGS. 1A-1B being processed by a urine sedimentation analyzer;

FIGS. 1D-1G depict additional aspects of a lid portion of the all-in-one specimen cup of FIGS. 1A-1C, as configured in accordance with the principles of the invention;

FIGS. 2A-2B depict one or more embodiments of a biological specimen analyzer configured to implement one or more aspects of the invention;

FIGS. 3A-3B depict one embodiment of a process for performing one or more aspects of the invention;

FIG. 5 depicts a screenshot from a biological specimen analyzer showing various test results generated in accordance with the principles of the invention.

DETAILED DESCRIPTION OF THE EXEMPLARY EMBODIMENTS

Overview of the Disclosure

Figure 1A:
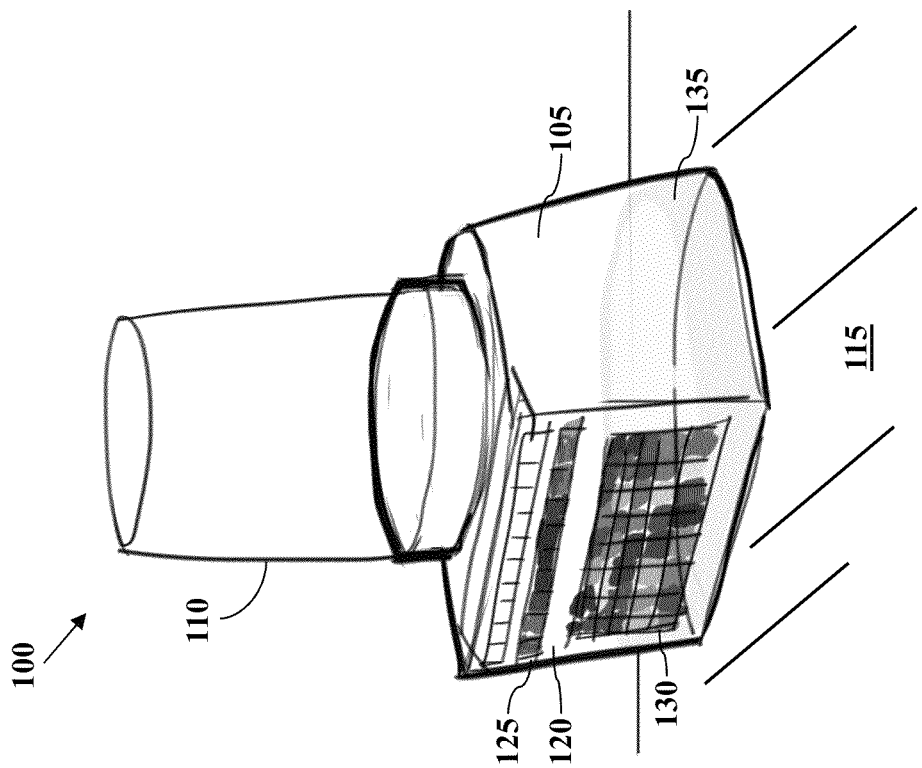
FIGS. 1A-1B depict various aspects of an all-in-one specimen cup configured according to the principles of the invention.

The present disclosure relates generally to performing color-based reaction testing of biological materials in an uncalibrated environment. More particularly, the present disclosure relates to an all-in-one specimen cup in which a biological material test strip (e.g., urine test strip) is affixed to a side of the cup, together with an adjacently-located reference color chart, so as to enable the use of a biological specimen analyzer to perform color-based reaction testing of such biological materials in an uncalibrated environment, i.e., using the same cup that was used to collect the biological sample. Specifically, a biological specimen analyzer may be used to capture one or more images of the test strip and adjacently-located reference color chart, both being affixed to a side of the cup.

The use of urine-type specimen cups can be used to treat numerous conditions and diseases. For example, kidney stone patients need to continuously monitor their pH levels. With this specimen cup, the pH strip may be placed/affixed to the all-in-one cup so that patients can easily determine their pH levels. Additionally, the all-in-one cup of the present disclosure can be used for early screening for diabetes. Patients concerned that they may be at risk for developing diabetes can use the novel disclosed all-in-one cup to screen for glucose in the urine since glucose can be used as an early indicator that one may have diabetes. As an early screen tool, patients can monitor their urine daily to see if they start to have glucose in the urine. If so, the test can then recommend that the patient get a real diabetes test done at their physician's office. Heretofore, performing such tests in the home with any acceptable level of accuracy and convenience has not been possible.

In certain embodiments, the image data specifically representing the individual test pads on the test strip, as well as the reference color blocks on the reference chart, are then located within the captured image, such as by using an image processing algorithm executed, at least in certain embodiments, by the biological specimen analyzer. Thereafter, the diagnostic client may compare the color data associated with each of the previously-located test pads with the corresponding color data for the reference color blocks. Since each test pad will have an associated test-specific sequence of color blocks on the reference chart organized in either a row or column, the color information for a given test pad need only be compared with its corresponding test-specific sequence of color blocks on the reference chart.

The above comparison operation may be performed to identify any color matches between the test pads and the corresponding sequences of reference color block. In certain embodiment, this color matching operation may be performed using a Lab color space analysis.

In any event, based on this comparison operation, a set of test results can be generated which effectively identifies which of the reference chart's color blocks most closely matches the color of the corresponding dipstick's test pads. Since each of the reference color blocks are associated with a particular test result (e.g., negative, positive, very positive, etc.), the actual test result corresponding to the matching color block may be readily determined, e.g., using a lookup table that correlates particular color blocks with corresponding test results. The generated test results may then be provided to the user in a printed or displayed form. Alternatively, the test results may simply be stored for later retrieval.

In this fashion, the novel methodology of the invention enables a single all-in-one specimen cup to be used for performing color-based reaction testing of biological materials in an uncalibrated environment, unlike the highly-calibrating conditions required by prior art systems. This advancement in the technological arts is made possible, at least in part, based on the fact that the color data associated with the reference color chart and the color data associated with the exposed test strip are equally impacted by the specific camera used and the specific ambient lighting conditions under which the data was collected. Therefore, the color data of the test strip is automatically normalized against the reference to which it needs to be compared (i.e., the reference chart), thereby rendering calibration unnecessary. This, in turn, enables virtually any user device, whether general- or special-purpose, that is equipped with a camera to be used in performing what was previously only possible using expensive and highly calibrated equipment. This would allow for mobile and even remote testing of biological materials (for example in rural villages and such) to be performed at both a low cost and with a higher accuracy and precision than manual inspection.

Additionally, the novel design of the all-in-one cup enables such test to be performed more conveniently by the patient themselves and/or more efficiently by processing laboratories.

As used herein, the terms "a" or "an" shall mean one or more than one. The term "plurality" shall mean two or more than two. The term "another" is defined as a second or more. The terms "including" and/or "having" are open ended (e.g., comprising). Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner on one or more embodiments without limitation. The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

In accordance with the practices of persons skilled in the art of computer programming, the invention is described below with reference to operations that are performed by a computer system or a like electronic system. Such operations are sometimes referred to as being computer-executed. It will be appreciated that operations that are symbolically represented include the manipulation by a processor, such as a central processing unit, of electrical signals representing data bits and the maintenance of data bits at memory locations, such as in system memory, as well as other processing of signals. The memory locations where data bits are maintained are physical locations that have particular electrical, magnetic, optical, or organic properties corresponding to the data bits.

When implemented in software, the elements of the invention are essentially the processor-executable code segments to perform the necessary tasks. The code segments can be stored in a "processor executable storage medium," which includes any medium that can store information. Examples of the processor executable storage mediums include an electronic circuit, a semiconductor memory device, a ROM, a flash memory or other non-volatile memory, a floppy diskette, a CD-ROM, an optical disk, a hard disk, etc.

Finally, when a test pad is described herein as being an "exposed" test pad, it means that the test pad has been in contact with, or otherwise exposed to either urine, blood, saliva, feces, sweat or any other biological materials.

Overview of All-in-One Specimen Cup

Figure 1B:
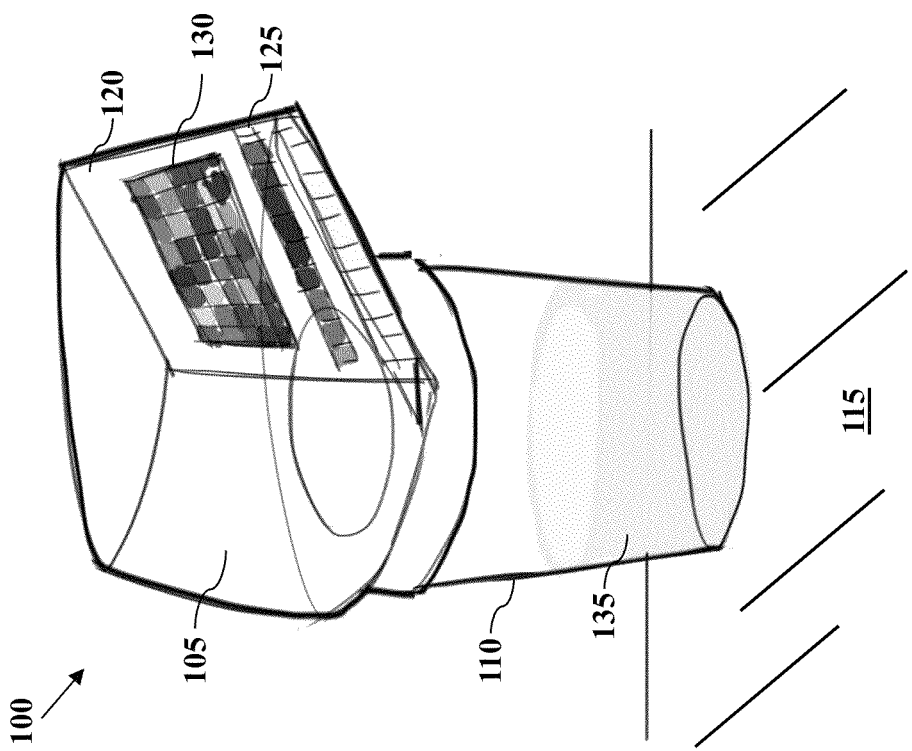

FIGS. 1A-1B depict an embodiment of an all-in-one specimen cup 100 configured in accordance with the principles of the invention. In particular, the cup 100 includes a lid portion 105 and a container portion 110. While the container portion 110 is shown as being in the shape of a cylindrical cup, it should equally be appreciated that the container portion 110 may be any size or shape capable of receiving biological samples.

The lid portion 105 is further shown as having a color-based reaction test strip 125 affixed to a flat side 120 of the lid portion 105 of the cup 100. The test strip 125 may comprise one or more reagent test pads that are chemically treated with a compound that is known to change color in the presence of particular reactants. The test strip 125 should preferably be affixed to an inside surface of the lid portion 105 so that it can be exposed to a biological specimen that is in the cup 100.

Additionally, a color reference chart 130 is shown as also being affixed to the flat side 120 and adjacent to the test strip 125. While the reference color chart 130 is shown as having multiple rows and columns to accommodate running multiple tests on a single sample, in the event that only one test is to be performed on the collected specimen, the reference color chart 130 may only consist of a single strip of reference colors. It should further be appreciated that the reference color chart 130 may be incorporated into the test strip 125 itself.

Although not shown, the lid portion 105 may also include a barcode identifying the particular test(s) for which the cup 100 was designed, i.e., the particular test for which the test strip 125 will test. The barcode may also, or alternatively, be used to identify the patient from whom the specimen was collected.

As shown, the lid portion 105 is attachable to the container portion 110, and the lid portion 105 is configured to close securely around the top edge of the container portion 110. When the cup 100 is sitting in the upright position, such as on the surface 115 of FIG. 1A, any previously-collected biological specimen 135 will collect in the container portion 110. Conversely, when the cup 100 is turned upside down, as shown in FIG. 1B, the previously-collected biological specimen 135 will flow from the container portion 110, through an opening in the base of the lid portion 105, and thereafter collect in the volume of the lid portion 105, as shown in FIG. 1B. The cup 100 is configured so that the test strip 125 is exposed to the biological specimen 135 when the cup 100 is turned from the upright position of FIG. 1A to the upside down position of FIG. 1B. In order to facilitate resting the cup 100 in the upside down position, the top of the lid portion 105 may be flat.

Referring now to FIG. 1C, depicted is an embodiment of the all-in-one specimen cup 100 as it is being processed by analyzing device 140, which configured to also perform urine sedimentation analysis. As is generally known, urine sedimentation levels may be analyzed by microscopic inspection of the urine sample itself. Currently, two different devices are required to perform both color-based reaction testing and urine sedimentation analysis. However, the novel configuration of the analyzing device 140, in combination with the configuration of the cup 100, makes it now possible to use a single device to perform both types of testing, and in a more accurate and efficient manner.

In order to perform the dual color-based reaction testing and urine sedimentation analysis, the analyzing device 140 is equipped with an L-shaped probe 145 through which liquid may be withdrawn. The L-shaped probe is configured to enter an aperture 150 arranged on a side of the lid portion 105 of the cup 100, as shown in FIG. 1C. The aperture 150 should be sealed or otherwise configured to allow only one-way passage in order to prevent the collected biological sample from escaping. For example, the aperture 150 may comprise a rubber-type material affixed into the side of the lid portion, which may itself be manufactured of a plastic or glass material. When the L-shaped probe 145 is configured with a sharp tip, such as a needle, the analyzing device 140 can mechanically operate the L-shape probe 145 to penetrate the aperture 150, withdraw a portion of the collected sample, and then be withdrawn out of the aperture 150, all without allowing any of the collected sample inside the lid portion 105 from escaping since the rubber-type material will naturally re-seal once the sharp end of the probe 145 is withdrawn out of it. A traditional urine sedimentation analysis may then be performed on the withdrawn specimen.

Additionally, the analyzing device 140 is also equipped with a camera 155, as shown in FIG. 1C. As will be explained in detail above, the camera 155 is oriented and configured to capture an image of the lid portion 105 of the cup; in particular, of the exposed test strip (e.g., test strip 125), together with an adjacently-located color reference chart (e.g., chart 130). The captured image may then be analyzed in accordance with the teachings set forth below with reference to FIGS. 4A-4C in order to carry out one or more color-based reaction tests on the collected specimen.

Referring now to FIGS. 1D-1F, depicted are various views of an exemplary lid portion 105 of an all-in-one specimen cup configured in accordance with the principles of the invention. With reference first to FIG. 1D, the lid portion 105 is configured with a lip 160 to form a liquid-tight seal with a container portion (e.g., container portion 110) of the cup 100. In addition, a base of the lid portion 105 is equipped with an opening 165 to allow a collected specimen to pass from the container portion into the lid portion 105 when the cup 100 is turned upside down, such as was shown in FIGS. 1A-1B above. While the opening 165 is shown as being crescent-shaped, it should be appreciated that the opening 165 may have any number of other configurations and still perform its intended function.

Referring now to FIG. 1E, the lid portion 105 may be usable in connection with a cap 170, as opposed to the container portion 110 of FIGS. 1A-1B. In this embodiment, a patient may provide a specimen through a larger version of opening 165 and directly into the lid portion 105 while it is in the upside down position, as shown in FIGS. 1D and 1E. The cap 170 may then be placed over the opening and secured to the lid portion 105 using any known means, e.g., using threads located either on the inside or outside of the lip 160. Alternatively, the cap 170 may simply 'snap' into place over the lip 160. In this fashion, the lid portion 105 may serve both the function of the container portion 110 in that it receives the specimen directly from the patient, as well as the function of exposing the test strip 125 to the received specimen. This arrangement may be more convenient since it eliminates the need for the separate container portion 110.

Referring now to both FIGS. 1F and 1G, an exemplary embodiment of a lid portion 105 of the all-in-one specimen cup 100 is shown. In particular, the lid portion 105 includes the above-described color-based reaction test strip 125 affixed to a flat side 120. Additionally, a color reference strip/chart 130 is shown as also being affixed to the flat side 120 and adjacent to the test strip 125. For simplicity, the reference color chart 130 in FIGS. 1F and 1G is shown as having only a single row. However, it should be appreciated that the reference color chart 130 would have multiple rows and columns when it is desirable to accommodate running multiple tests on a single sample, such as shown in FIGS. 1A-1B and FIGS. 4A-4C. Of course, if only one test is to be performed on the collected specimen, then it would be appropriate to have only a reference color chart 130 with a single strip of reference colors.

In addition to having the opening 165 described above, the embodiment of the lid portion 105 in FIGS. 1F and 1G also comprises a collecting ledge 175 which may be used to more precisely direct the collected specimen towards the test strip 125 as the cup 100 is being turned upside down. As shown, the collecting ledge 175 is coupled to the flat side 120 of the lid portion 105. The collecting ledge 175 begins at an area adjacent to the test strip 125 along an inner surface of the flat side 120, and extends in a sloping manner radially inward to at least partially cover (extend across) the opening 165. In this fashion, when the lid portion 105 is secured to a container portion (not shown) and is turned upside down, a collected specimen in the container portion will pass through the opening 165 under the force of gravity and immediately impact the collecting ledge 175, which will in turn divert the specimen outwardly along its length and towards the test strip 125 disposed on the inner surface of the flat side 120, thereby ensuring that the test strip 125 is properly exposed to the specimen. The collecting ledge 175 may similarly be used with embodiments of the lid portion 105 which utilize the cap 170 of FIG. 1E.

FIGS. 2A-2B depict one or more embodiments of a biological specimen analyzer 200 configured to implement one or more aspect of the invention. The analyzer 200 may be any device configured to analyze the color-based test results on a test strip (e.g., test strip 125). While in the embodiment of FIG. 2B, the analyzer 200 is shown as being a smartphone-type device, the analyzer 200 may similarly be a dedicated, standalone analyzer, such as analyzer 140 of FIG. 1C.

In any event, the biological specimen analyzer 200 may include a display 210, such as a liquid crystal display or any other known type of display usable in connection with such an electronic user device. The analyzer 200 may also include a user input 220, which may include one or more buttons or keys in the form of a keypad, number pad, keyboard or any other collection of individual keys, buttons or the like. In another embodiment, the user input 220 may be integrated with the display 210 in the form of a touchscreen.

The analyzer 200 preferably also includes a processor 230 and a camera 240. The camera 240 may be based on CCD technology or Complementary metal-oxide-semiconductor (CMOS) image sensor technology, or based on any other known type of image-capturing technology.

Finally, the analyzer 200 is shown as having memory 250 which, among other programs, software modules, data and operating system files, stores a diagnostic software client 260. When the client 260 is loaded from memory 250 and executed by processor 230, it performs one or more aspects of the invention, as more fully detailed below with respect to FIGS. 3A-3B.

FIG. 2B depicts the specimen analyzer 200 in the form of a smartphone-type device in which display 210 functions as both a display screen, as well as a portion of the user input 220 by virtue of being a touchscreen.

Referring now to FIGS. 3A-3B, depicted is one embodiment of a process 300 for carrying out one or more aspects of the invention. In certain embodiments, process 300 may be performed by a biological specimen analyzing device, such as the analyzing device 140 of FIG. 1C or analyzer 200 of FIGS. 2A-2B, although other electronic devices may be similarly configured and programmed to perform the computer-implemented operations of process 300. While process 300 may be applied in the context of urinalysis, it should equally be appreciated that process 300 may be carried in the contexts of testing other biological materials as well, such as blood, saliva, feces and sweat.

As shown in FIG. 3A, process 300 begins at block 310 with the diagnostic program (e.g., client 260) being initiated on the specimen analyzing device. Thereafter, at block 320 a test strip (e.g., test strip 125) would be exposed to a subject's biological specimen (e.g., urine). In one embodiment, this may be accomplished by first having the patient provide a urine specimen into a container portion (e.g., portion 110) of an all-in-one cup (e.g., cup 100). A lid portion (e.g., portion 105) may then be affixed to the container portion, and then the assembled cup may be turned upside down, such as in the position shown in FIG. 1B. Once turned upside down, the previously-collected biological specimen may flow from the container portion, through an opening (e.g., opening 165) in the lid portion, and into the lid portion. In the lid portion, a test strip (e.g., strip 125), with the help of an optional collecting ledge (e.g., ledge 175), may be exposed to the collected biological specimen.

In embodiment which utilize a cap (e.g., cap 170) rather than a separate container portion, the operation of block 320 may simply comprise having the patient provide a specimen through directly into the base of the lid portion 105 (e.g., through opening 165) while it is in the upside down position, e.g., as shown in FIGS. 1D and 1E above. As with the embodiment described above, as the specimen is provided directly into the lid portion, the test strip may be exposed to the collected biological specimen. This may be accomplished with the help of the optional collecting ledge (e.g., ledge 175). The cap may then be placed over the opening and secured to the lid portion using any known means. However, since the lid portion will already be in the upside down position after the specimen has been provided, in this embodiment there will be no need to turn the assembled cup (lid portion and cap) upside down.

In any event, the now-exposed test strip will have been affixed to a flat side (e.g., flat side 120) of the lid portion and in a position adjacent to a reference color chart (e.g., reference chart 130), such as in the arrangement of FIGS. 1A-1B. Accordingly, at block 330 a single image of the test strip, together with the adjacently-located reference color chart, may be captured by the specimen analyzing device. It should be appreciated that the device may be preferably equipped with a CCD or CMOS camera (e.g., camera 155 or 240) for use in capturing the image at block 330. In an alternative embodiment, the test strip and reference color chart may be photographed at different times rather than as a single image, so long as the ambient photographing conditions are essentially the same.

Moreover, it is preferably the case that the image capturing operation of FIG. 3A be performed in an uncalibrated environment, as would have been necessary with prior art systems requiring highly-calibrating conditions. As previously described, this advancement in the technological arts is made possible since the color data associated with the reference color chart and the color data associated with the exposed test strip are equally impacted by the specific camera used and the specific ambient lighting conditions under which the data was collected. Therefore, the color data of the test strip is automatically normalized against the reference to which it needs to be compared (i.e., the reference chart), thereby rendering calibration unnecessary.

Once the image data has been captured, process 300 continues to block 340 of FIG. 3B where the captured image data may be processed. Namely, the image data specifically representing the individual test pads on the exposed test strip, as well as the reference color blocks on the reference chart, must be first located within the captured image by an image processing algorithm of the diagnostic client (block 340). As will be described in more detail below with references to FIGS. 4A-4C, this may be done using a template matching operation in which the captured image data may be compared against a reference in order to identify common patterns or features. Alternatively, a 'shape location' algorithm, such as the 'square algorithm' included in the OpenCV (Open Source Computer Vision) software package, may be used. In general terms, such 'shape location' or similar algorithms are based on analyzing image data for the occurrence of distinct edges or transitions as a way to identify the position of specific features of interest. It should be appreciated, however, that other known image processing means may be similarly used to locate the image data representing the individual test pads on the exposed test strip, as well as the reference color blocks on the reference chart.

Once the operation of block 340 has been completed, process 300 may then continue to block 350 where an image data comparison operation is carried out. In particular, the diagnostic program compares the color data associated with each of the previously-located test pads with the similarly-located color data for the reference color blocks. For example, and as will be described in more detail below with reference to FIGS. 4A-4C, each test pad will have an associated test-specific sequence of color blocks on the reference chart organized in either a row or column. This test-specific sequence of color blocks includes all of the possible different colors that the reagent on the test pad is chemically capable of producing when exposed to reactants. Therefore, a given test pad need only be compared with this corresponding test-specific sequence of color blocks.

The goal of this comparison operation is to identify color matches between the test pads and the corresponding sequences of reference color block. This color matching operation comprises performing a color space analysis on image data—the particularly-identified image data from block 340 above. Although the RGB color space is typically what would be used in such computer-implemented systems, another aspect of the invention is to rather use the Lab color space for performing the comparison or matching operation of block 350. In the RGB color space, each pixel has a 'red' component, a 'green' component, and a 'blue' component which, when mixed together, produces the colors we see on a computer screen. In contrast, however, the Lab color space is a color-opponent space with dimension L for lightness, and dimensions a and b for the color-opponent dimensions.

Due to differences between the way computers analyze color data and the way the human eye processes colors, there are some circumstances in which computers may interpret the RGB color space differently than one would expect. In the context of color-based reaction testing, in particular, the inventor has found that using the Lab color space rather than the RGB color space produces more accurate results.

Based on the comparison operation of block 350, process 300 will generate a set of test results at block 360. That is, the comparison operation of block 350 will effectively identify which of the reference chart's color blocks most closely matches the color of the corresponding test pads. Since each of the reference color blocks are associated with a particular test result (e.g., negative, positive, very positive, etc.), the test result corresponding to the matching color block may be easily generated (block 360). By way of a non-limiting example, a lookup table stored in memory (e.g., memory 250) that correlates particular color blocks with corresponding test results may be used. Thereafter, process 300 ends.

Additionally, however, once generated the test results may be provided to the user, and it should further be appreciated that such test results may be provided in any form, including printed or displayed. Alternatively, the test results may simply be stored for later retrieval.

In this fashion, the novel methodology of the invention enables color-based reaction testing of biological materials to be performed in an uncalibrated environment. This enables virtually any user device, whether general- or special-purpose, that is equipped with a camera to be used in performing what was previously only possible using expensive and highly calibrated equipment. This would allow for mobile and even remote testing of biological materials (for example in rural villages and such) to be performed at both a low cost and with higher levels of accuracy and precision than manual inspection.

It should further be appreciated that the uncalibrated image capturing operation of block 330 above may be performed in any number of ways or environments.

Figure 4A:
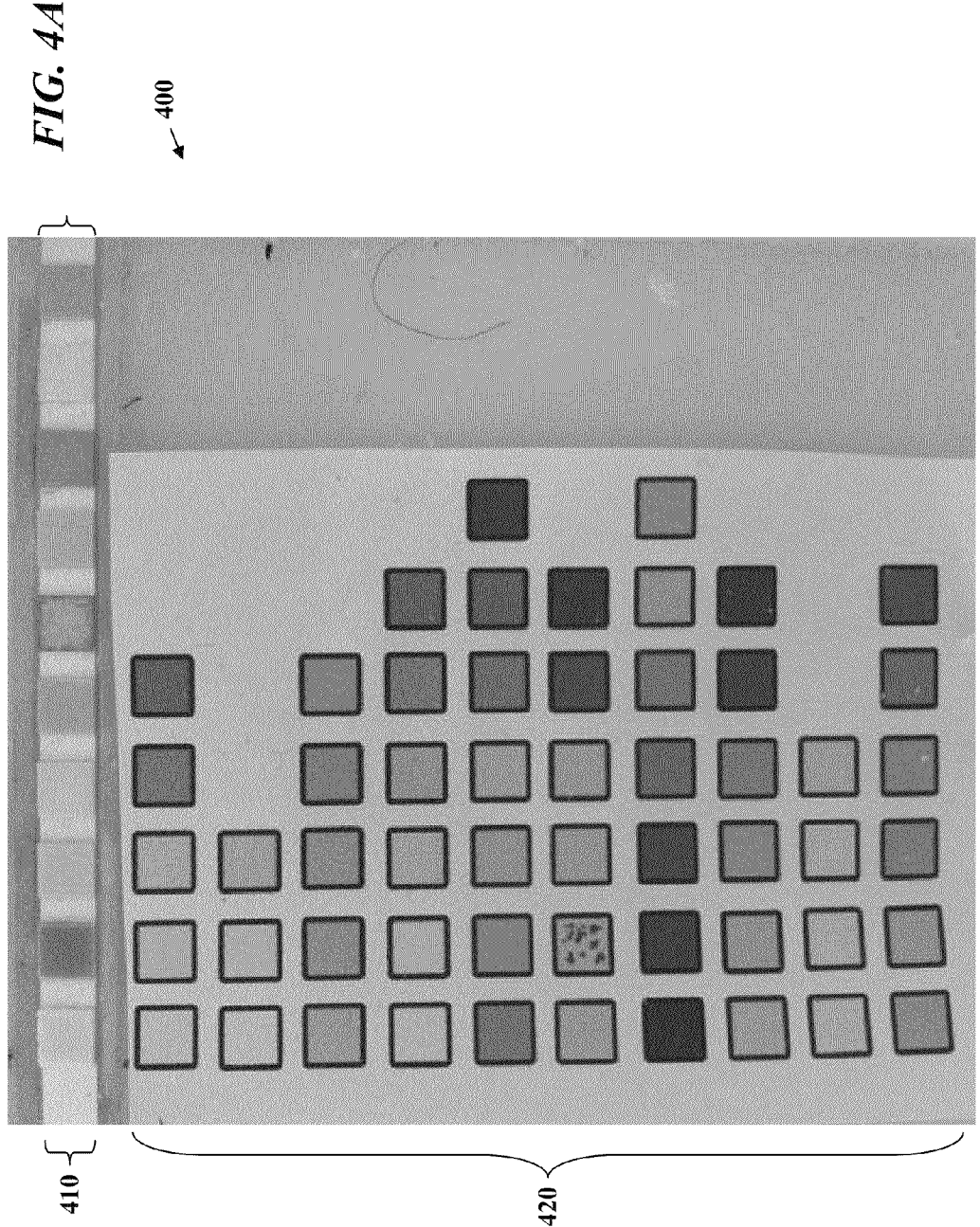
FIGS. 4A-4C depict images taken by a biological specimen analyzer usable in connection with the principles of the invention.

Referring now to FIG. 4A, depicted is a one embodiment of a captured image 400, such as the captured image described above with reference to block 330 of FIG. 3A. As shown in FIG. 4A, the exposed test strip 410 (e.g., test strip 125) was positioned near the reference color chart 420 (e.g., chart 130) and the combination of the two photographed together by a specimen analyzing device equipped with a camera (e.g., analyzing device 140 of FIG. 1C or analyzer 200 of FIGS. 2A-2B). While the example of FIGS. 4A-4C are not shown as being affixed to a side of a lid portion (e.g., portion 105) of an all-in-one cup, such as cup 100, it should be appreciated that all of the details set forth below are equally applicable to the test strip 125 and reference color chart 130 of FIGS. 1A-1B, including how the individual test pads and reference colors are located and/or processed.

Figure 4B:
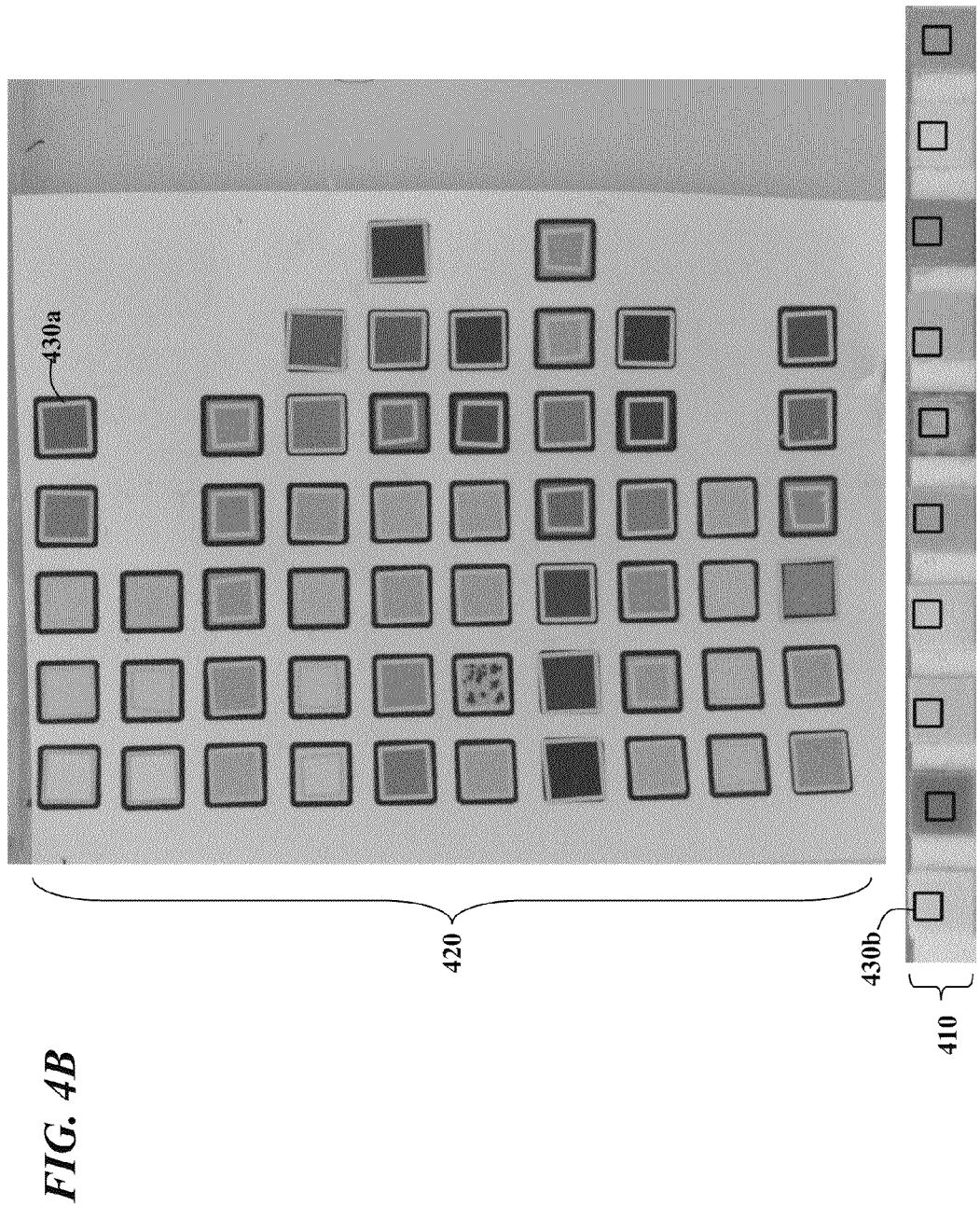
Figure 4C:
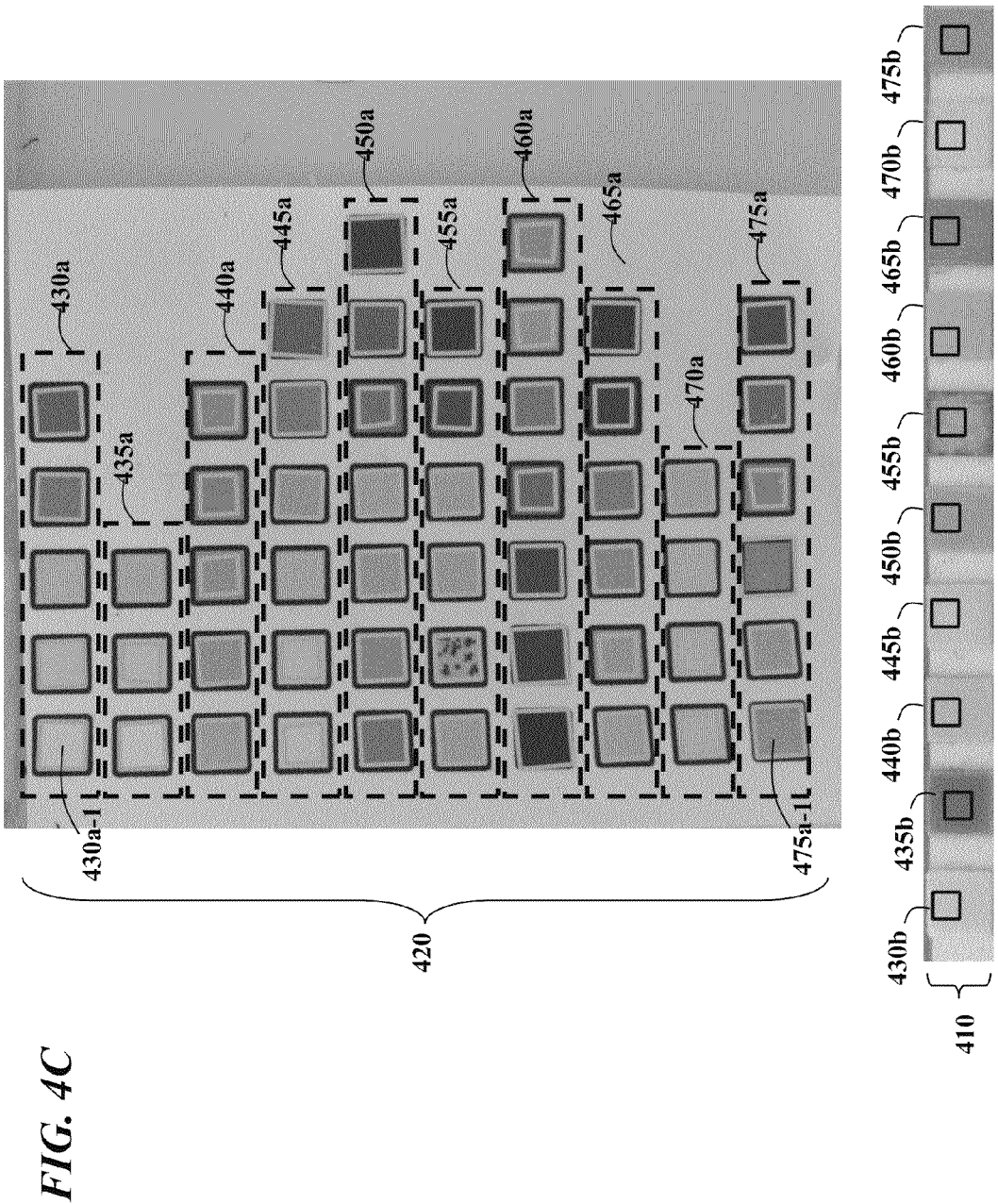

FIG. 4B depicts one embodiment of how the captured image 400 may then be processed to locate the image data corresponding to the individual test pads and reference color blocks, as described above with reference to block 340 of FIG. 3A. In particular, and as shown in FIG. 4B, a shape location algorithm (see e.g., OpenCV) has been applied to the reference color chart 420. A black border has been added to each of the reference color blocks in order to enhance the algorithm's ability to detect the edges of the individual color backs of chart 420. The successful identification of a color block is reflected in each case by a 'square marker,' such as green square marker 430a shown in FIG. 4B. While this identification data may be displayed to the user so that the user can verify that the reference color blocks have been properly identified, in other embodiments this operation may be a background process.

Referring to the test strip 410 now, rather than using a shape location algorithm, the individual test pads are located using a template matching operation in which the captured image data corresponding to the test strip 410 is directly compared against a reference image of a test strip. With template matching, each pad is located based, at least in part, on matching the captured image data of the test strip 410 to a known pattern of a test strip and to interpolate the location of individual test pads based on expected position.

Once located, a representative area on each of the test pads may be identified. For example, as shown in FIG. 4B, the color image data contained within the area defined by square 430b may be used as the image data corresponding to the first pad of test strip 410. Similarly, areas within each of the subsequent test pads may be defined and used in the color matching operation to follow (e.g., comparison operation of block 350 of FIG. 3B).

While FIG. 4B was described as having used template matching to locate the test pads on test strip 410 and a shape location algorithm for locating the color blocks of reference chart 420, it should equally be appreciated that either technique may be used in either case. Similarly, other known image processing means may also be used.

Once the locations of the individual test pads on the test strip 410 have been located using either template matching, a shape location algorithm, etc., it may be preferable to average the color data within the defined area (e.g., square 430b) so as to account for minor color variations from point-to-point. While the color blocks of the reference chart may similarly be averaged, it is less likely that there will be significant color variation within the reference color blocks.

Referring now to FIG. 4C, depicted is one embodiment of how the comparison operation, as described above with reference to block 350 of FIG. 3B, may be performed. In particular, the color blocks of reference color chart 420 are shown as being grouped into separate color block sequences 430a-475a. Correspondingly, the image data for each of the individual test pads of the test strip 410 have been identified as test pad areas 430b-475b. As previously described, each test pad need only be compared with the corresponding color blocks that it is capable of matching. Moreover, since the reference chart 420 is organized into individual rows, where each row corresponds to the detection of a particular substance or cellular material, each test pad area (430b-475b) need only be compared with its corresponding color block sequence 430a-475a. For example, the color data of test pad area 430b would only be compared with each of the color blocks in sequence 430a, the test pad area 435b would only be compared with each of the color blocks in sequence 435a, and so forth.

As initially described above with reference to block 350, this comparison operation will result in identifying, for each test pad area (430b-475b), which of the reference chart's color blocks most closely matches. Then, lookup operation may be performed to identify the particular test result (e.g., negative, positive, very positive, etc.) that corresponds to that particular reference color block. For example, in the case of test pad area 430b, the closest match was determined to be color block 430a-1. The known test results that correspond to that color block would then be found in a table, stored in memory, etc. Additionally, and by way of example only, for test pad area 475b the closest match was determined to be color block 475a-1. Again, the test results (e.g., negative, positive, very positive, etc.) that correspond to color block 475a-1 could then be looked up.

Again, it should be equally appreciated that the test strip 125 and reference color chart 130 of FIGS. 1A-1B may be similarly substituted in for the reference color charts and test strips described above with reference to FIGS. 4A-4C.

In any event, once the test result data has been obtained for each of the test pads, the results may be reported to the user in any number of formats. FIG. 5, for example, depicts one embodiment of a screenshot 500 that may be displayed to a screen of a specimen analyzing device summarizing the results of the test associated with each of the test pads.

Rather than capturing a combined image with both the exposed test strip, as well as the reference color chart, photographs of a series of reference color charts may be captured under varying ambient conditions as an alternative way of implementing the invention. Such images may be stored for later comparison to exposed test strips.

By way of example, after an image of an exposed test strip has been captured, the ambient conditions under which that exposed test strip was captured may be determined and then compared to the varying ambient conditions under which the previously-stored reference color charts were captured. The stored reference chart that was taken under conditions most closely approximating those under which the exposed test strip was taken would then be used for the image data comparison operation of block 350, as described above.

Various modification and adaptations to the above disclosure would be equally within the scope of the invention. For example, other known image processing means may be similarly used to mark the image data representing the individual test pads on the exposed test strip, as well as the reference color blocks on the reference chart. Also, rather than individual reference color blocks, a continuous color spectrum may be used so as to provide more precise test results.

It should further be appreciated that since all of the biological material test results are automatically captured by the analyzing device itself, such data can be easily exported and/or manipulated. For example, it would be possible to e-mail test results directly to patients or other healthcare providers. Similarly, results may be uploaded directly to an online health information system, a laboratory information system, or the like. Moreover, test results may be graphed over time so as be able to track patient health.

The ease of use, portability and calibration-independent nature of the invention allows color-based reaction testing of biological materials, such as urine, to be performed even by the patients at home.

In one or more additional embodiments of the invention, principles of the invention may be extended to perform urine sedimentation analysis by attaching or integrating a microscope lens to the camera of the user device. The resulting image data may be similarly analyzed using the methodologies disclosed herein.

Overview of All-in-One Diaper

In another embodiment, color-based reaction testing of biological materials in an uncalibrated environment may be performed in connection with an all-in-one diaper test in which a biological material test strip (e.g., urine test strip) is affixed to a diaper, together with an adjacently-located reference color chart, so as to conveniently enable the testing of an infant's urine using a highly accurate technique. The use of a diaper configured in accordance with the principles of the invention can be used to detect dehydration in infants, for example, or any other known condition or disease which tends to manifest itself in an infant's urine or feces.

In certain embodiments, it may be preferable to design the all-in-one diaper for only a single test. In that case, the test strip would comprise a single test pad treated with the appropriate reagent, and the reference color chart would be a color reference strip comprising all of the possible colors that the test pad may assume. Such a test pad and color reference strip may preferably be integrated into a single strip which may then be affixed to the inner lining of a diaper using any known means, so long as the test pad can contact and react with the infant's urine or feces while being worn. Additionally, the test pad and reference color strip should be either removable from the diaper or visible in the diaper, for purposes of capturing an image thereof.

In other embodiments, the test pad may be comprised of a series of test pads, each chemically treated to test for different conditions. In such embodiments, the color reference strip would be a color reference chart with a series of rows, each of which would contain a series of reference color blocks corresponding to the various test pads.

Regardless of whether a single or multiple specimen tests are to be run, an analyzing device (e.g., analyzer 200) may be used to perform color-based reaction testing of an infant's biological specimen using the diaper itself, and in an uncalibrated environment, i.e., at home. For example, the above-mentioned analyzer 200 may be used to capture one or more images of the test strip/pad and adjacently-located reference color chart/strip, both being affixed to the inside of a diaper, and then processed in accordance with the process 300 of FIGS. 3A-3B and using the same image processing principles set forth above with respect to FIGS. 4A-4C.

In this fashion, the novel methodology of the invention enables a single all-in-one diaper test to be performed on an infant's urine or feces in an uncalibrated environment, unlike the highly-calibrating conditions required by prior art systems. Additionally, the novel design of the all-in-one diaper enables such test to be conveniently performed without concern of whether the diaper will absorb the entire urine sample, and in the comfort of the home.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. Trademarks and copyrights referred to herein are the property of their respective owners.

What is claimed is:

1. A method for color-based reaction testing of biological materials comprising the acts of:

capturing, by an electronic device using ambient lighting in an uncalibrated environment, digital image information of an exposed test strip and of a reference color chart, wherein the digital image information of each of the exposed test strip and the reference color chart is captured in the same uncalibrated environment, wherein the exposed test strip comprises a plurality of test pads, and wherein further the reference color chart comprises a plurality of color blocks;

locating, by a diagnostic software application that is executing on the electronic device, first image data within the digital image information corresponding to each of the plurality of test pads, said first image data having uncalibrated color information;

locating, by the diagnostic software application executing on the electronic device, second image data within the digital image corresponding to the plurality of color blocks on the reference color chart, said second image data having uncalibrated color information;

matching, by the diagnostic software application executing on the electronic device, uncalibrated color information from the first image data to corresponding uncalibrated color information from the second image data, wherein said matching comprises comparing uncalibrated color information corresponding to a first test pad of the plurality of test pads to uncalibrated color information from at least one of the plurality of color blocks on the reference color chart;

generating, by the diagnostic software application executing on the electronic device, test results based on said matching; and displaying, on a display screen of the electronic device, a graphical representation of the test results indicating an absence, presence and degree of presence of a reactant within the biological specimen.

2. The method of claim 1, wherein locating first image data comprises applying, by the diagnostic software application executing on the electronic device, one of a shape location algorithm and a template matching operation to the first image data.

3. The method of claim 2, wherein locating second image data comprises applying, by the diagnostic software application executing on the electronic device, one of the shape location algorithm and the template matching operation to the second image data.

4. The method of claim 1, further comprising averaging, by the diagnostic software application executing on the electronic device, color information across the first image data, and wherein matching the color information comprises matching the averaged color information for the first image data to corresponding color information from the second image data.

5. The method of claim 1, wherein the digital image information for each of the exposed test strip and the reference color chart is captured in a single digital image.

6. The method of claim 1, wherein the digital image information for each of the exposed test strip and the reference color chart is captured under the same ambient photographing conditions, but at different times.

7. The method of claim 1, wherein matching further comprises matching, by the diagnostic software application executing on the electronic device, color information from the first image data to corresponding color information from the second image data by performing Lab color space analysis on the color information from the first and second image data.

8. The method of claim 1, wherein the electronic device is a mobile smartphone-type device.

9. The method of claim 1, wherein the plurality of color blocks comprising the reference color chart are arranged in a plurality of test-specific sequences.

* * * * *

UNITED STATES PATENT AND TRADEMARK OFFICE
CERTIFICATE OF CORRECTION

| | |
|---|---|
| PATENT NO. | : 8,877,140 B2 |
| APPLICATION NO. | : 13/914194 |
| DATED | : November 4, 2014 |
| INVENTOR(S) | : Stephen L. Chen et al. |

It is certified that error appears in the above-identified patent and that said Letters Patent is hereby corrected as shown below:

On the Title Page

Item (60), Line 1, delete "No. 60/409,922," and insert --No. 61/409,922,--.

Signed and Sealed this
Tenth Day of September, 2024

Katherine Kelly Vidal
*Director of the United States Patent and Trademark Office*